(12) United States Patent
Barbic et al.

(10) Patent No.: US 8,170,316 B2
(45) Date of Patent: May 1, 2012

(54) TOMOGRAPHIC IMAGING WITH A STRIPE-LIKE SHAPED SENSOR

(75) Inventors: Mladen Barbic, Ashburn, VA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 882 days.

(21) Appl. No.: 12/243,830

(22) Filed: Oct. 1, 2008

(65) Prior Publication Data

US 2009/0087064 A1    Apr. 2, 2009

Related U.S. Application Data

(60) Provisional application No. 60/997,140, filed on Oct. 1, 2007.

(51) Int. Cl.
*G06K 9/00* (2006.01)
(52) U.S. Cl. .......................... 382/131; 382/132
(58) Field of Classification Search ........... 382/131–132
See application file for complete search history.

(56) References Cited

U.S. PATENT DOCUMENTS

| | | | |
|---|---|---|---|
| 5,761,331 A * | 6/1998 | Clark, III | 382/131 |
| 6,341,156 B1 * | 1/2002 | Baetz et al. | 378/98.8 |
| 6,813,374 B1 * | 11/2004 | Karimi et al. | 382/131 |
| 7,120,226 B2 * | 10/2006 | Ledoux et al. | 378/57 |
| 2005/0033173 A1 | 2/2005 | Von Behren et al. | |
| 2005/0078784 A1 | 4/2005 | Francke | |
| 2005/0111612 A1 | 5/2005 | Ikhlef et al. | |
| 2007/0060816 A1 | 3/2007 | Simpkin | |
| 2008/0130974 A1 * | 6/2008 | Xu et al. | 382/131 |

OTHER PUBLICATIONS

PCT/US08/78495 International Search Report and Written Opinion. Feb. 13, 2009.

* cited by examiner

*Primary Examiner* — Bhavesh Mehta
*Assistant Examiner* — Utpal Shah
(74) *Attorney, Agent, or Firm* — Canady & Lortz LLP; Bradley K. Lortz

(57) ABSTRACT

Tomographic imaging using an imaging sensor that has a stripe-like shape is disclosed where a stripe sensor is mechanically scanned over a sample at different angles. For a single stripe detector imaging, linear motion and angular rotation are required. Single stripe sensor imaging may be performed using an elongated inductive coil detector. By utilizing an array of parallel stripe sensors that can be individually addressed, two-dimensional imaging can be performed with rotation only, eliminating the requirement for linear motion, e.g. with parallel coils array. Imaging with a stripe-type sensor of particular width and thickness (where width is much larger than thickness) is resolution limited only by the thickness (smaller parameter) of the sensor. Multiple sensor families can be produced where this imaging technique may be beneficial such as magneto-resistive, inductive, SQUID, and Hall effect sensors, and particularly in the field of magnetic resonance imaging (MRI).

28 Claims, 16 Drawing Sheets

TOMOGRAPHIC IMAGING WITH A STRIPE-LIKE SHAPED SENSOR

CROSS-REFERENCE TO RELATED APPLICATIONS

This application claims the benefit under 35 U.S.C. §119(e) of the following U.S. provisional patent application, which is incorporated by reference herein:

U.S. Provisional Patent Application No. 60/997,140, filed Oct. 1, 2007, and entitled "METHOD OF TOMOGRAPHIC IMAGING WITH A STRIPE-LIKE SHAPED SENSOR", by Barbic et al.

STATEMENT OF GOVERNMENT RIGHTS

The U.S. Government has certain rights in this invention pursuant to Grant No. HG026440 awarded by the National Institutes of Health and Grant No. DMR0349319 & 0622228 awarded by the National Science Foundation.

BACKGROUND OF THE INVENTION

1. Field of the Invention

This invention relates to sensors. Particularly, this invention relates to sensor techniques for tomographic imaging.

2. Description of the Related Art

Imaging of samples through projections has been an important concept ever since the discovery of x-rays, and has been used in the gravitational theory and radio astronomy before becoming widespread through computerized tomography in x-ray, electron, and optical imaging, among others. See e.g., A. Cormack, J. Appl. Phys. 34, 2722 (1963); G. Hounsfield, British J. Radiol. 46, 1016 (1973); D. J. de Rosier arid A. Klug, Nature (London) 217 130 (1968); and D. E. Kuhl and R. Q. Edwards, Radiol. 80, 653 (1963). The first report of magnetic resonance imaging (MRI) had its roots in image reconstruction from projections. See, P. C. Lauterbur, Nature (London) 242, 190 (1973). Computerized tomographic image reconstruction algorithms for conventional radiation-based tomography are by now well developed and can be easily transferred to novel imaging methodologies such as the one described in this disclosure on stripe sensor tomography. See e.g, G. T. Herman, Image Reconstruction from Projections, Academic Press, New York (1980); F. Natterer, The Mathematics of Computerized Tomography, John Wiley & Sons, New York (1986); A. C. Kak and M. Slaney, Principles of Computerized Tomographic Imaging SIAM, Philadelphia (2001); S. R. Deans, Tile Radon Transform and Some of Its Applications, Krieger Publishing Company, Malabar (1993); and P. T. Callaghan, Principles of Nuclear Magnetic Resonance Microscopy, Oxford University Press. New York (1991), which are incorporated by reference herein.

The various disciplines of scanning probe microscopy conventionally employ a point-by-point raster scanning of the sample in the x-y plane as a common way of obtaining a two-dimensional image of the sample. However, it can frequently be the case that the scanning sensor is not of the point type, but is instead of the stripe shape, typically due to the thin-film lithographic character of sensor fabrication. For example, in scanning magneto-resistance microscopy the imaging sensor is a thin film magneto-resistive element of small thickness, t, and much larger width, w. See, S Y. Yamamoto and S. Schultz. Appl. Phys. Lett. 69, 3263 (1996). By raster scanning of this sensor in the x-y plane, a two-dimensional image of a magnetic sample can be obtained. See also, S. Y. Yamamoto, R. O'Barr, S. Schultz, and A. Scherer, IEEE Trans. Magn. 33, 1016 (1997); M. Todorovic, S. Schultz, J. Wong, and A. Scherer, Appl. Phys. Lett. 74, 2516 (1999); and M. Barbic, S. Schultz, J. Wong, and A. Scherer, IEEE Trans. Magn. 37, 1657 (2001). There has been a perceived notion in such reports that two-dimensional images obtained with a stripe-type magneto-resistive sensor are limited in spatial resolution by thickness, t, in the x-direction, and width, w, in the y-direction.

In view of the foregoing, there is a need in the art for apparatuses and methods for more efficient apparatuses and methods for tomographic imaging, e.g. using stripe-like sensors. In addition, there is a need for such apparatuses and methods that can deliver high spatial resolution with reduced scanning requirements. There is further a need for such imaging apparatuses and methods that can operate more quickly and efficiently than conventional techniques. These and other needs are met by the present invention as detailed hereafter.

SUMMARY OF THE INVENTION

Tomographic imaging for the case of an imaging sensor that has a stripe-like shape is disclosed. Surprisingly, there is a common analytical principle between two-dimensional tomography using conventional electromagnetic or particle radiation and tomography where a stripe sensor is mechanically scanned over a sample at different angles. For a single stripe detector imaging, linear motion and angular rotation are required. Single stripe sensor imaging may be performed using an elongated inductive coil detector. By utilizing an array of parallel stripe sensors that can be individually addressed, two-dimensional imaging can be performed with rotation only, eliminating the requirement for linear motion, e.g. with parallel coils array. Imaging with a stripe-type sensor of particular width and thickness (where the width is much larger than the thickness) is resolution limited only by the thickness (smaller parameter) of the sensor. Multiple sensor families can be produced where this imaging technique may be beneficial such as magneto-resistive, inductive, SQUID, and Hall effect sensors, and particularly in the field of Magnetic Resonance Imaging.

A typical apparatus embodiment of the invention comprises a radiation source for directing radiation comprising information of a sample, one or more stripe sensor elements, each having a width substantially greater than a thickness, for generating a plurality of one-dimensional projection scan signals of the sample, each of the one-dimensional projection scan signals generated from the directed radiation received by the one or more stripe sensor elements at a distinct relative angle, and one or more computing devices for deriving a tomographic image of the sample by combining the plurality of one-dimensional projection scan signals of the sample. Deriving the tomographic image of the sample may comprise calculating a Fourier transform of the plurality of one-dimensional projection scan signals, multiplication by a ramp function in conjugate space followed by an inverse transformation, and finally integration over all angles. Typically, the one or more stripe sensor elements each provide substantially equal sensitivity along the width. The received radiation may comprise information of the sample by reflection from the radiation source off the sample, by transmission from the radiation source across the sample, or by emission where the sample comprises the radiation source itself.

Embodiments of the invention may be implemented with stripe sensor elements of various types. For example, the one or more stripe sensor elements may be thin film magneto-resistive sensors, asymmetric superconducting interference devices (SQUIDS), nuclear magnetic resonance (NMR) elongated micro-fabricated waveguides and stripelines, planar asymmetric micro-Hall detectors or microwave near-field slit probes. In one exemplary embodiment of the invention, the one or more stripe sensor elements each comprise an elongated inductive coil loop including two substantially parallel conductors.

In some embodiments of the invention, the one or more stripe sensor elements are scanned linearly across the sample at each distinct relative angle to generate each of the plurality of one-dimensional scan signals of the sample. In some embodiments of the invention, the one or more stripe sensor elements may comprise a plurality of adjacent stripe sensor elements in a linear array each adjacent along the width. Each of the plurality of the one-dimensional projection scan signals may be generated by sequentially sensing the plurality of adjacent stripe sensor elements at the distinct relative angle. (This can eliminate the need to linearly scan the one or more stripe sensor element across the sample.) In one notable example, each of the plurality of adjacent stripe sensor elements of the linear array may comprise an elongated inductive coil loop including two substantially parallel conductors and the adjacent stripe sensor elements share a common conductor of the two substantially parallel conductors.

A typical method embodiment of the invention may comprise the steps of directing radiation comprising information of a sample from a radiation source, generating a plurality of one-dimensional projection scan signals of the sample, each of the one-dimensional projection scan signals generated from the directed radiation received by one or more stripe sensor elements at a distinct relative angle, each of the one or more stripe sensor elements having a width substantially greater than a thickness, and deriving a tomographic image of the sample by combining the plurality of one-dimensional projection scan signals of the sample with one or more computing devices. Deriving the tomographic image of the sample may comprises the steps of calculating a Fourier transform of the plurality of one-dimensional projection scan signals, multiplying the Fourier transform by a ramp function in conjugate space, performing an inverse transformation on the multiplied Fourier transform, and integrating the inverse transformed multiplied Fourier transform over all angles. Method embodiments of the invention may be further modified consistent with the apparatuses and systems described herein.

For example, directing the radiation may comprise reflecting the radiation from the radiation source off the sample such that the received radiation comprises the information of the sample. Alternately, the radiation may be transmitted from the radiation source across the sample such that the received radiation comprises the information of the sample. The radiation may also be emitted from the sample such that received radiation from the sample itself comprises the information of the sample.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

Embodiments of the present improve over the various conventional disciplines of scanning probe microscopy where a point-by-point raster scanning of the sample in the x-y plane is a common way of obtaining a two-dimensional image of the sample. Embodiments of the present invention recognize that it can frequently be the case for such techniques that the scanning sensor may be not of the point type, but having a stripe shape, typically due to the thin film lithographic character of many sensor fabrication techniques. For example, in the scanning magnetoresistance microscopy, the imaging sensor is a thin film magnetoresistive element of small thickness t and much larger width w. By raster scanning of this sensor in the x-y plane, a two-dimensional image of a magnetic sample can be obtained. There has been a perceived notion in those reports that two-dimensional images obtained with a stripe-type magnetoresistive sensor are limited in spatial resolution by thickness t in the x direction, and width w in the y direction. It is an object of the present disclosure to show that by linear scanning motion of the stripe-type sensor at different angular orientations combined with the tomographic imaging principles, two-dimensional images of samples can be obtained that are limited in spatial resolution along both x and y axes by only the thickness t, i.e., the smaller parameter of the sensor. See, S. Y. Yamamoto and S. Schultz, Appl. Phys. Lett. 69, 3263 1996; S. Y. Yamamoto, R.

O'Barr, S. Schultz, and A. Scherer, IEEE Trans. Magn. 33, 3016 1997; M. Todorovic, S. Schultz, J. Wong, and A. Scherer, Appl. Phys. Lett. 74, 2516 1999; and M. Barbic, S. Schultz, J. Wong, and A. Scherer, IEEE Trans. Magn. 37, 1657 2001, which are incorporated by reference herein.

Some embodiments of the invention may employ linear scanning motion of one or more stripe-type sensor elements at different angular orientations to generate multiple one-dimensional projections that are combined with tomographic imaging principles to yield a two-dimensional image of a sample that are limited in spatial resolution along both x- and y-axes by only the thickness, t, i.e. the smaller parameter, of the sensor. Other embodiments of the invention may forego linear scanning through implementation of an array of stripe sensor elements where each one-dimensional projection is generated by sequentially sensing each stripe sensor element of the array. Stripe sensor element techniques described herein may be applied across a range of sensor types, provided they are amenable to a stripe-like configuration exhibiting a substantially uniform sensitivity response along the width of the sensor.

2. Single Stripe Sensor Imaging

Figure 1A:
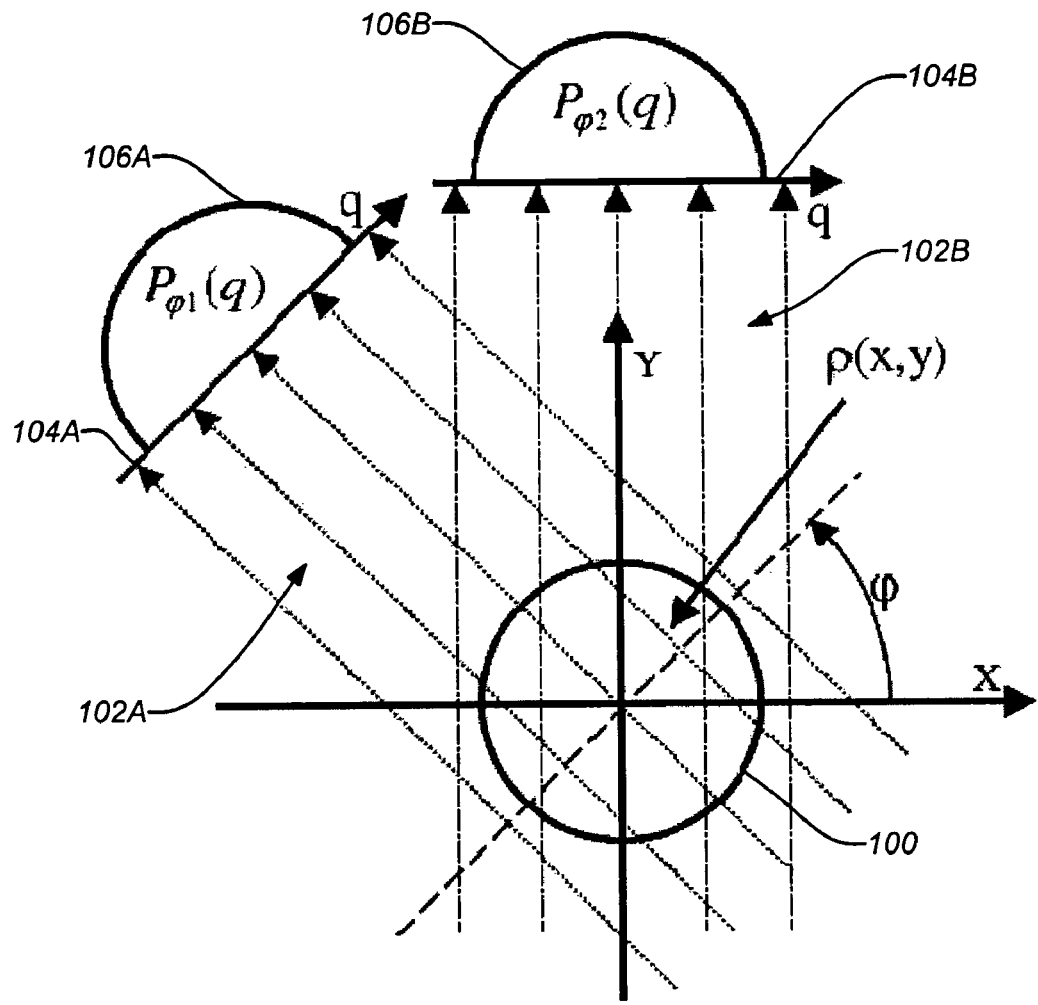
FIG. 1A illustrates a convention computerized tomographic imaging technique.
Figure 1B:
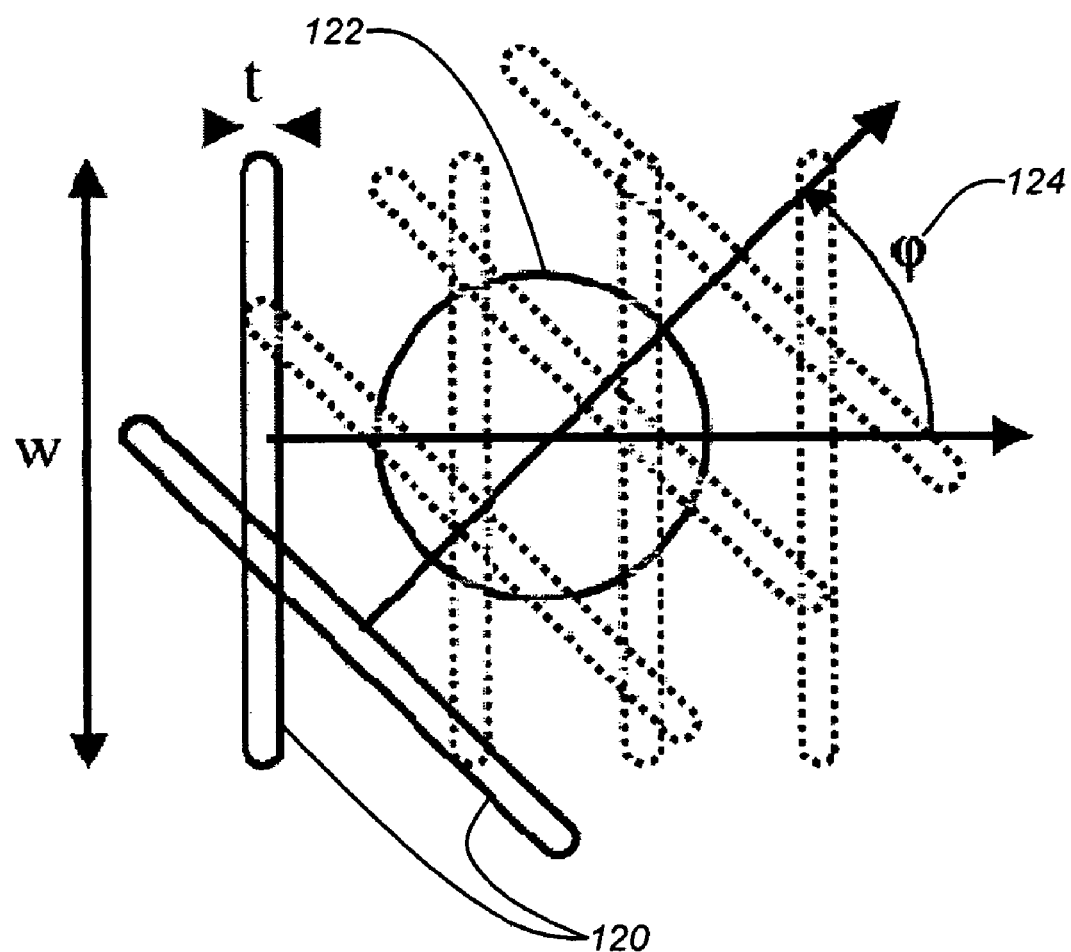
FIG. 1B illustrates a novel stripe sensor computerized tomographic imaging technique.

FIGS. 1A & 1B illustrate conventional radiation-based two-dimensional tomography and tomography where a stripe sensor is mechanically scanned over a sample at a sequence of different angles. FIG. 1A shows the schematic representation of a conventional tomography configuration for imaging a sample 100 with the parameters used in the image reconstruction process indicated. Radiation 102A, 102B comprising uniformly separated parallel rays (electromagnetic or particle) from a radiation source (not shown) is used to obtain an image projection 106A, 106B along an axis at a detector 104A, 104B (indicated by the position of the q axis) on the opposite side of the radiation source at different angles, φ. For each projection 106A, 106B, a one-dimensional Radon transform of the sample density function ρ(x, y) is formed:

$$P_\phi(q) = \int_{(\phi,q)line} \rho(x, y) ds \quad (1)$$

By obtaining multiple one-dimensional Radon transforms 106A, 106B from Equation (1) at the different angles, φ, image reconstruction is performed by the Fourier transform filtered back-projection algorithm for parallel projections:

$$P(x, y) = \int_0^\pi \left\{ \int_{-\infty}^{+\infty} \left[ \int_{-\infty}^{+\infty} P_\phi(q) \cdot e^{i2\pi kq} dq \right] |k| e^{-i2\pi kq} dk \right\} d\phi \quad (2)$$

See A. C. Kak and M. Slaney, "Principles of Computerized Tomographic Imaging SIAM, Philadelphia (2001), which is incorporated by reference herein. This reconstruction process involves calculation of the Fourier transform of the Radon transform (the inner-most bracketed term), multiplication by a ramp function |k| in conjugate space followed by an inverse transformation (outer bracketed term), and finally integration over all angles for the completion of the image reconstruction (outermost integration term). Note that the detector 104A, 104B may be repositioned to the different angles, φ or multiple detectors 104A, 104B may be used.

FIG. 1B is schematic diagram showing operation of stripe sensor tomography in accordance with an embodiment of the invention. In this case, a linear stripe sensor element 120 of width, w, and thickness, t, (having the width substantially greater than the thickness) is mechanically scanned over a sample 122 that extends over a region that is smaller than the width of the stripe sensor element 120. (Note that the overall sample 122 may actually be larger than the width of the stripe sensor element 120, but the scanned portion of the sample 122 will be limited to the width of the stripe sensor element 120.) Typically, the stripe sensor element 120 may have equal sensitivity along its width, w, (as is assumed in this description), and each single line scan of the stripe sensor element 120 will result in the one-dimensional data that represents a one-dimensional projection of the two-dimensional sample. By scanning the stripe sensor element 120 across the sample 122 at different angles φ 124 as shown in FIG. 1B (or equivalently by rotating the sample 122 to the line at various angles φ and scanning the stripe sensor element 120 along the same line) multiple one-dimensional projections of the two-dimensional sample represented by Equation (1) are obtained and may be stored as will be understood by those skilled in the art. Finally, by utilizing the reconstruction process of Equation (2) on the stored multiple one-dimensional projections, which may be implemented with one or more computing devices (e.g., a programmed computer or dedicated hardware computing device), a two-dimensional tomographic image of the sample can be generated as further described with respect to FIGS. 3A & 3B. Note that although only two one-dimensional projection scans are illustrated in FIG. 1B (separate by the angle φ), additional one-dimensional projection scans at other distinct relative angles applied in the algorithm of Equation (2) will improve the imaging results.

Figure 1C:
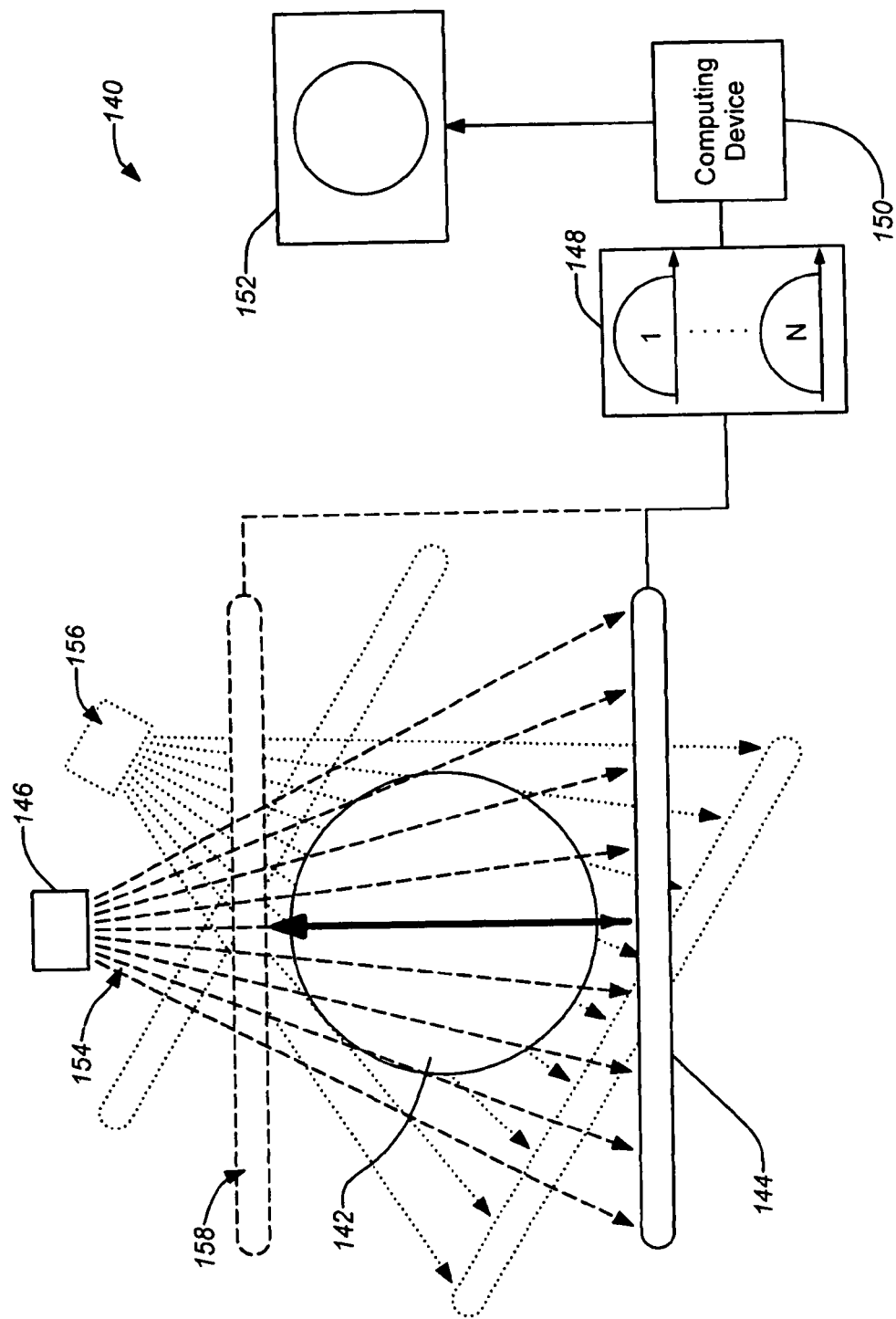
FIG. 1C is a schematic diagram of an exemplary tomographic imager embodiment of the invention.

FIG. 1C is a schematic diagram of an exemplary tomographic imager embodiment of the invention. The imager 140 comprises a radiation source 146 for emitting radiation 154 across a sample 142. The stripe sensor element 144 has a width substantially greater than its thickness and is used to generate a plurality of one-dimensional projection scan signals 148 of the sample 142. Each of the one-dimensional projection scan signals 148 is generated from the radiation received by the stripe sensor element 144 as the sensor element 144 is linearly scanned over the sample 142 from first to a second position 158 in the direction of the indicated arrow.

As shown in FIG. 1C, the radiation source 146 emits radiation 154 across a sample 142 to be received by the stripe sensor element 144. However, those skilled in the art will appreciate that it is only necessary that radiation 154 that comprises information of the sample 142 is directed to be received by the stripe sensor element 144. The type and definition of the applied radiation 154, e.g., particle or electromagnetic, power, wavelength, etc., will vary depending upon the particular application as will be understood by those skilled in the art. Embodiments of the invention may be implemented in different configurations are possible including a transmission, reflection, and emission configuration. FIG. 1C illustrates another example of a transmission configuration where a separate radiation source 154 emits radiation 154 across a sample 142 to impart information of the sample 142 to the radiation 154. (Note that the radiation source 154 is shown on one side of the stripe sensor element 144 in FIG. 1C, however, the radiation source will typically be disposed behind the sample 142 in a typical transmission configuration as described below in FIG. 1D.)

Each of the additional one-dimensional projection scan signals 148 is generated at a distinct relative angle. This may be accomplished by repositioning the stripe sensor element 144 (and possibly the radiation source 146) relative to sample 142 (e.g., as shown by the second position 156 for the stripe sensor element 144 and radition source 146 in phantom which would yield a second one-dimensional projection scan signal). Alternately, the sample 142 may be repositioned relative to the stripe sensor element 144 (and possibly the radiation source 146). In any case, each one-dimensional projection scan signal (e.g., scans signals 1 to N) 148 corresponds to a linear scan made at a distinct relative angle. The plurality of one-dimensional projection scan signals 148 are processed to derive the tomographic image 152 of the sample 142.

The plurality of one-dimensional projection scan signals 148 are provided to one or more computing devices 150, which apply the algorithm previously described and combine the plurality of one-dimensional projection scan signals 148 to derive a tomographic image 152 of the sample 142. Any suitable computing device 150, e.g., a programmed computer or dedicated hardware computing device, may be used to drive the sensor element and/or process the plurality of one-dimensional projection scan signals 148 to derive a tomographic image 152 as will be understood by those skilled in the art. Thus, the one or more computing devices 150 calculate a Fourier transform of the plurality of one-dimensional projection scan signals 148, multiply this by a ramp function in conjugate space, perform an inverse transformation, and finally integrate over all angles.

Figure 1D:
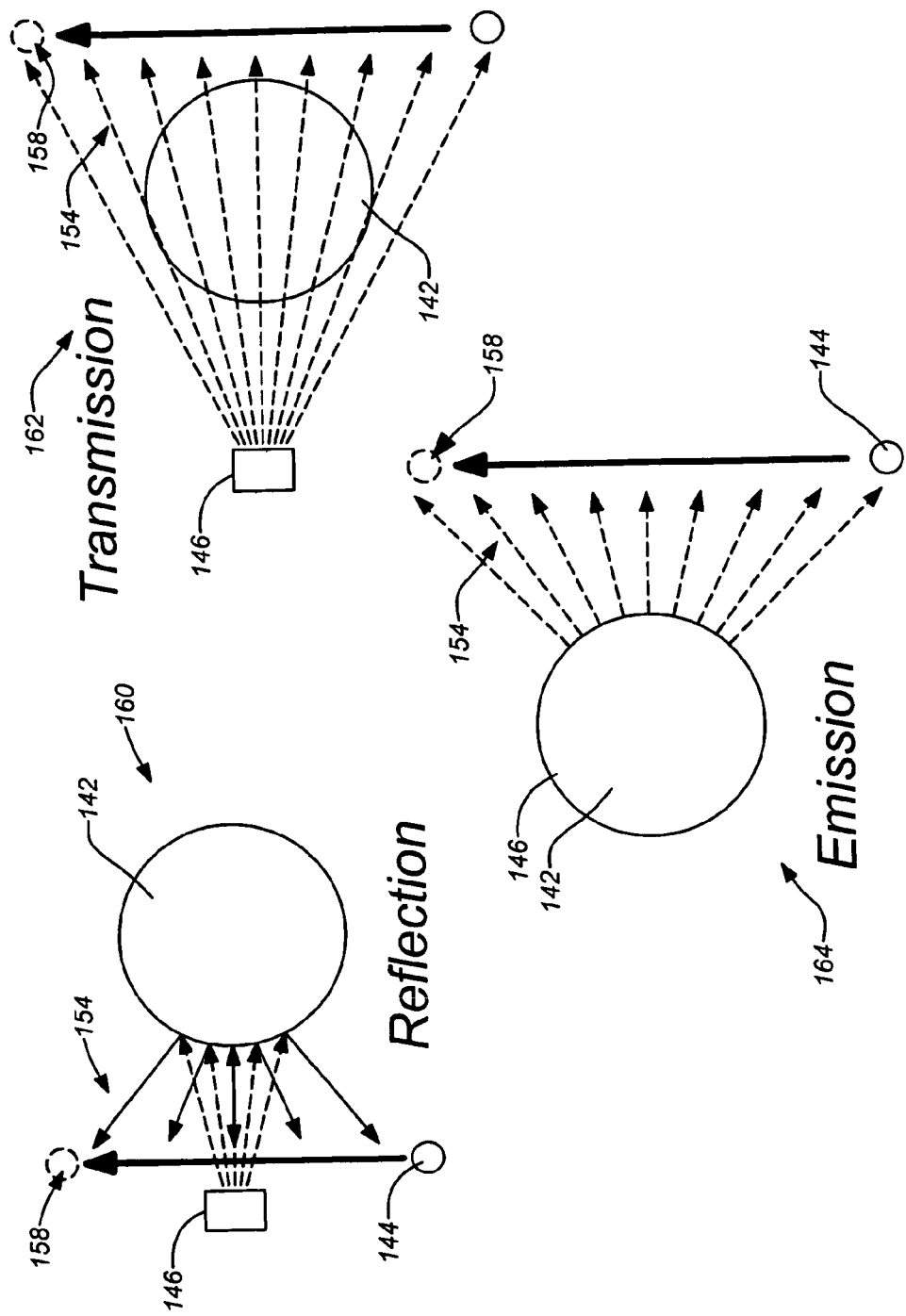
FIG. 1D illustrates a generalized transmission, reflection and emission configuration for an embodiment of the invention using a stripe sensor element.

FIG. 1D illustrates generalized reflection, transmission, and emission configurations 160, 162, 164, for an embodiment of the invention using a stripe sensor element 144. In a reflection configuration 160, the radiation source 146 is substantially co-located with the stripe sensor element 144 (i.e., on the same side of the sample 142). In this case, information of the sample 142 is imparted to the radiation 154 as a consequence of it being reflected off the sample 142 and back to the stripe sensor element 142. In a transmission configuration 162, information of the sample 142 is imparted to the radiation 154 as emitted from the source 146 across the sample 142 to the stripe sensor element, e.g., on the opposite side of the sample. Finally, in an emission configuration 164 the sample 142 itself is also the radiation source 146. Radiation 154 emitted from the sample 142 surface inherently comprises information of the sample 142.

The inventive principle is common in each of the example configurations 160, 162, 164 as will be understood by those skilled in the art. Each employs a stripe sensor element 144 to generate a plurality of one-dimensional projection scan signals of the sample from the directed radiation received by the stripe sensor element 144 (each at a distinct relative angle). As illustrated, the one-dimensional projection scan signals are generated as the stripe sensor element 144 is linearly scanned from the first position to the second position 158. In each configuration 160, 162, 164, the received radiation 154 comprises information of the sample 142, although the information may be acquired through different processes, reflection off the sample, transmission through the sample, or emission from the sample. Each of the described configurations 160, 162, 164, may employ one or more computing devices to derive a tomographic image of the sample operating in the same manner as the imager 140 of FIG. 1B. As previously mentioned, the particular radiation and sensor types, as well as the specific parameters of the configuration will depend upon the particular application, as will be understood by those skilled in the art.

The imaging apparatus in accordance with an embodiment of the invention in any configuration may employ a range of sensor element types. For example, the stripe sensor element may comprise an elongated inductive coil loop including two substantially parallel conductors as will be described in detail hereafter. Those skilled in the art will appreciate that analogous imaging systems may be readily developed for other sensor elements applying the described principles including thin film magneto-resistive sensors, asymmetric superconducting interference devices (SQUIDS), nuclear magnetic resonance (NMR) elongated micro-fabricated waveguides and stripelines, planar asymmetric micro-Hall detectors and microwave near-field slit probes. The particular type of the radiation source 146 and arrangement with the sensor element 144 will depend upon the specific application.

Figure 2A:
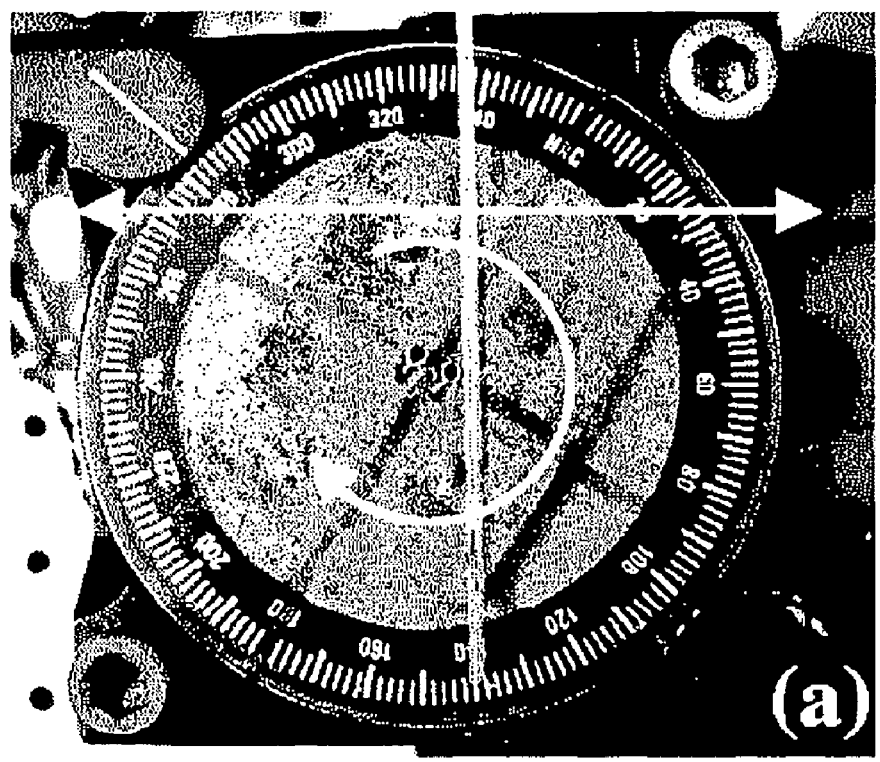
FIG. 2A is an example embodiment of the invention employing an elongated inductive coil loop.
Figure 2B:
FIG. 2B illustrates the test sample for the elongated inductive coil loop embodiment of the invention.

A example tomographic imaging apparatus embodiment of the invention may include a stripe sensor element that comprises an elongated inductive coil loop detector, shown in FIG. 2A. This example structure provides simplicity and has potential use in single sided magnetic resonance imaging or eddy current non-destructive evaluation as will be understood by those skilled in the art. See, e.g., B. Blumich, "NMR Imaging of Materials," Oxford University Press, New York (2000), which is incorporated by reference herein. The example coil may be made from two parallel conductors inserted into capillary tubes for insulation and disposed having a uniform separation of t=750 µm. The loop may be mounted on a linear mechanical translation stage with the axis of the linear motion indicated by the arrowed line in FIG. 2A. The tested "sample" to be scanned for imaging may comprise a circular coil pair, each approximately 1.5 mm in diameter, representing two point sources separated by a distance slightly larger than the thickness, t, of the sensor but much smaller than the width, w, of the sensor. The sample is mounted on the mechanical rotation stage visible in the figure. The magnified view of the two loop sources and the two conductors of the inductive stripe-like coil detector are shown in FIG. 2B. The sources may be driven in phase with an approximately 100 mA AC electric current electrical signal at approximately 11 kHz from an audio power amplifier (e.g., Teach Spin Model PAA1-A) driven by a lock-in amplifier signal source (e.g., Stanford Research Systems Model SR830). Due to the low output impedance of the stripe coil sensor, the detected signal may be coupled to a low-noise transformer pre-amplifier (Stanford Research Systems Model SR554) followed by the signal input channel of the lock-in amplifier. The loop may be scanned in 250 µm steps at 500 µm height above the sample surface. The rotation stage may be rotated by approximately 10 degrees after each linear scan.

Figure 3A:
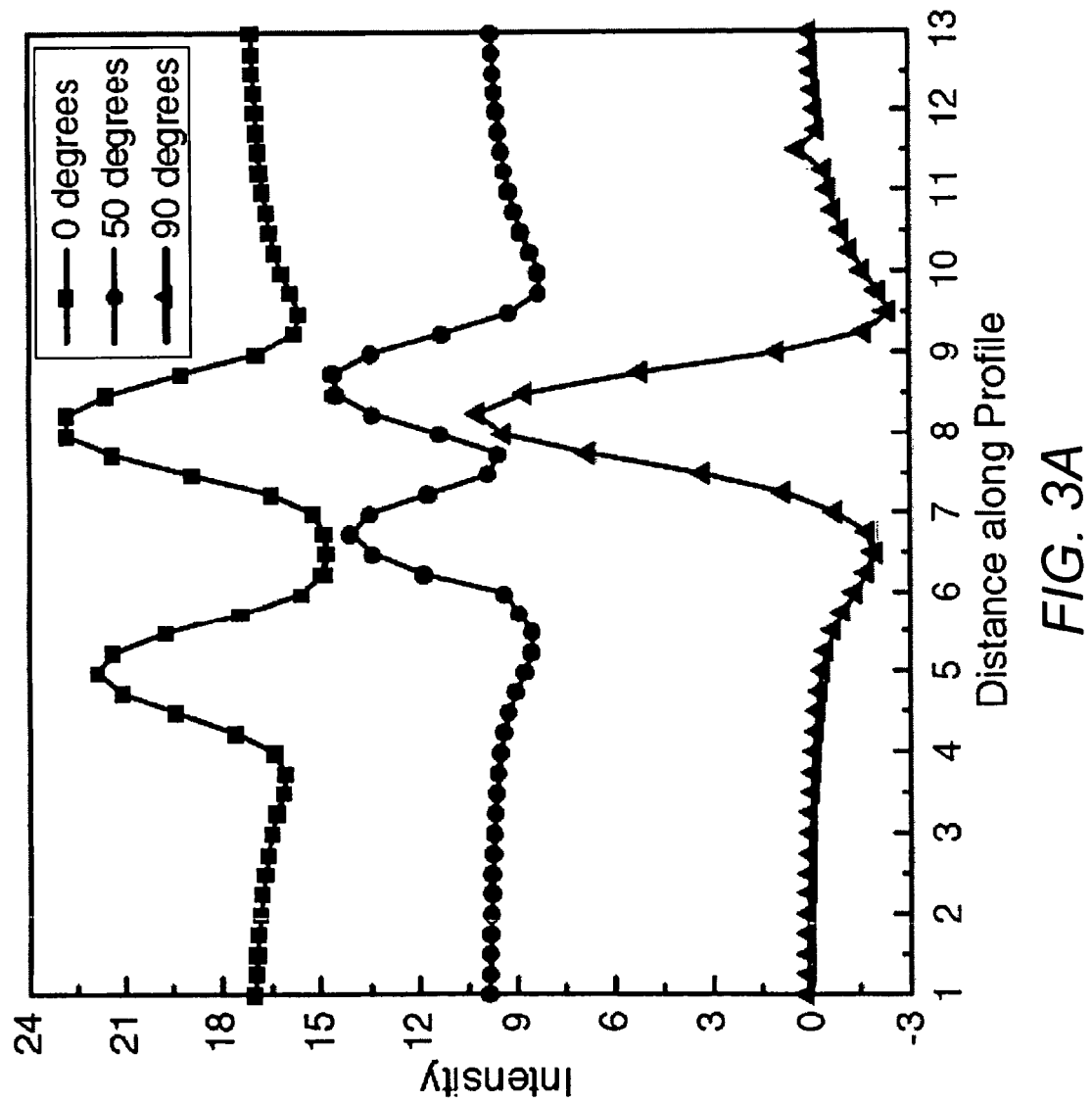
FIG. 3A shows a plot of three line scans representing one-dimensional projections of a two-dimensional sample from an example embodiment of the invention.

FIG. 3A shows three one-dimensional projection scans (of 18 total in this example) representing three different one-dimensional projections of a two-dimensional sample at different angular orientations. At zero degrees, the two sources are clearly resolved as indicated in graph, and at 90 degrees only a single large peak is detected, as expected for two in-phase AC sources concurrently under the detector.

Figure 3B:
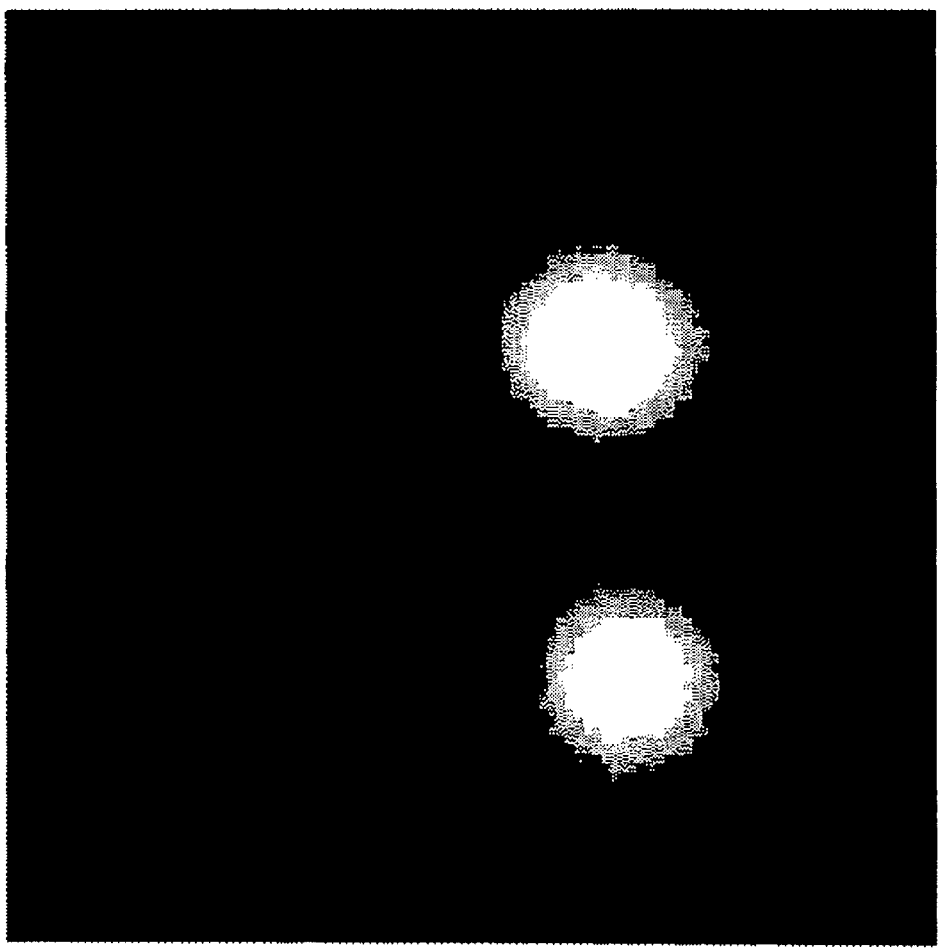
FIG. 3B is a two-dimensional image of the sample from an example embodiment of the invention.

FIG. 3B shows the resulting two-dimensional image of the sample (from 18 example projections) using the formalism of tomographic filtered back-projection image reconstruction of Equation (2) applied as described above. The two sources are clearly resolved, and the main argument that the two-dimensional image resolution is limited in both directions by only the narrow thickness parameter of the sensor is demonstrated.

It should be noted that a unique feature of this technique, as related to potential use in MRI, is that the imaging may be performed without the need for external high power gradient magnetic fields typically employed in MRI. In the stripe sensor case, the imaging resolution would be determined by the sensor thickness, and not by the gradient field values that could be achieved from external current carrying conductors.

3. Stripe Sensor Element Array Imaging

Figure 4A:
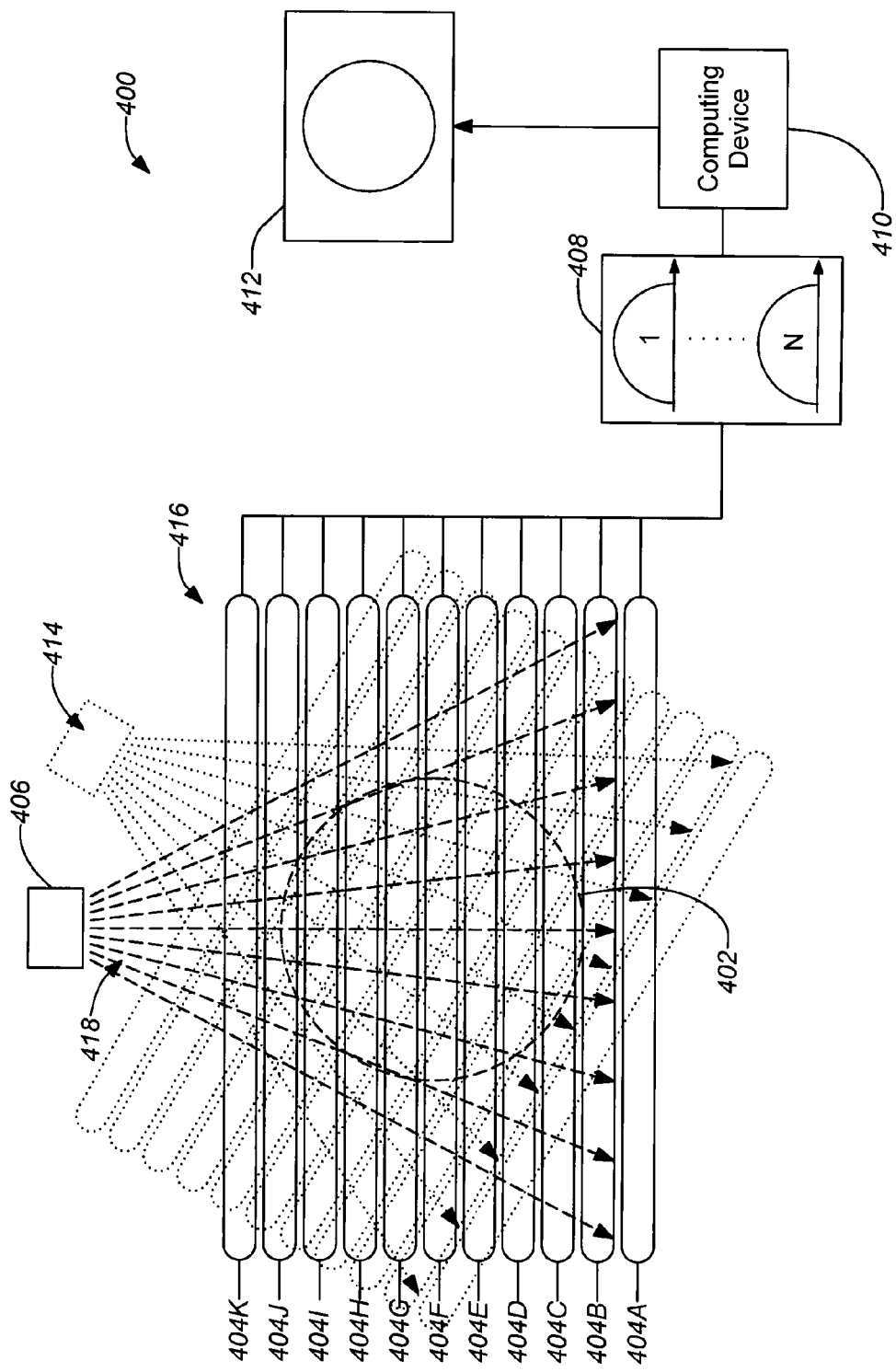
FIG. 4A illustrates and example apparatus for tomographic imaging employing an array of stripe sensor elements.

FIG. 4A illustrates an example imager apparatus 400 for tomographic imaging employing an array 416 of stripe sensor elements 404A-404K. Here, the principle of stripe-type sensor two-dimensional tomography previously described is further extended to two-dimensional imaging using a sensor array 416. This imager 400 generally operates in the same manner as the imager 140 of FIG. 1C. Thus, the imager 400 comprises a radiation source 406 for emitting radiation 416 across a sample 402. The type and definition of the applied radiation 418, e.g., particle or electromagnetic, power, wavelength, etc., will vary depending upon the particular application as will be understood by those skilled in the art.

The stripe sensor array 416 in this imager 400 comprises a plurality of stripe sensor elements 404A-404K. Each has a width substantially greater than its thickness. In this case, the plurality of one-dimensional projection scan signals 408 of the sample 402 are generated by sequentially sensing the plurality of stripe sensor elements 404A-404K. Each of the one-dimensional projection scan signals 408 is generated from the radiation emitted across the sample and received by the array 416 as the plurality of stripe sensor elements 404A-404K are sequentially sensed.

Here also, each of the additional one-dimensional projection scan signals 408 is generated at a distinct relative angle. This may be accomplished by repositioning the stripe sensor array 416 (and possibly the radiation source 406) relative to sample 402 (e.g., as shown by the second position 414 for the stripe sensor array 416 and radition source 406 in phantom which yields a second one-dimensional projection scan signal). Alternately, the sample 402 may be repositioned relative to the stripe sensor array 416 (and possibly the radiation source 406). In any case, each one-dimensional projection scan signal (e.g., scans signals 1 to N) 408 corresponds to sequential sensing of the elements 404A-404K of the array 416 made at a distinct relative angle. The plurality of one-dimensional projection scan signals 408 are processed to derive the tomographic image 412 of the sample 402 in the same manner as those of the imager 140 of FIG. 1C.

The plurality of one-dimensional projection scan signals 408 are provided to one or more computing devices 410, which apply the algorithm previously described and combine the plurality of one-dimensional projection scan signals 408 to derive a tomographic image 412 of the sample 402. Any suitable computing device 410, e.g., a programmed computer or dedicated hardware computing device, may be used to drive the sensor element and/or process the plurality of one-dimensional projection scan signals 408 to derive a tomographic image 412 as will be understood by those skilled in the art. Thus, the one or more computing devices 410 calculate a Fourier transform of the plurality of one-dimensional projection scan signals 408, multiply this by a ramp function in conjugate space, perform an inverse transformation, and finally integrate over all angles.

Embodiments of the invention employing a stripe sensor element array may also be implemented in any of the configurations 160, 162, 164, reflection, transmission, and emission, previously described in FIG. 1D. In each configuration 160, 162, 164, the single stripe sensor element 144 is replaced with an array spanning the distance from the first position of the element 144 to the second position 158 as described in FIG. 4A. The common inventive principle of each of the example configurations 160, 162, 164 is applicable to the stripe sensor array as well as will be understood by those skilled in the art. Each can employ a stripe sensor array to generate a plurality of one-dimensional projection scan signals of the sample from the directed radiation received by the stripe sensor array from sequential sensing of the elements (each scan taken at a distinct relative angle). The received radiation 154 comprises information of the sample 142 in every configuration 160, 162, 164, although the information may be acquired through different processes, reflection off the sample, transmission through the sample, or emission from the sample. Each of the described configurations 160, 162, 164, may employ one or more computing devices to derive a tomographic image of the sample operating in the same manner as the imagers 140, 400 of FIGS. 1B and 4A. As previously mentioned, the particular radiation and sensor types, as well as the specific parameters of the configuration will depend upon the particular application, as will be understood by those skilled in the art.

The imaging apparatus using a stripe sensor array in any configuration may employ a range of sensor element types. For example, the stripe sensor element may comprise an elongated inductive coil loop including two substantially parallel conductors as will be described in detail hereafter. Those skilled in the art will appreciate that analogous imaging systems may be readily developed for other sensor elements applying the described principles including thin film magneto-resistive sensors, asymmetric superconducting interference devices (SQUIDS), nuclear magnetic resonance (NMR) elongated micro-fabricated waveguides and stripelines, planar asymmetric micro-Hall detectors and microwave near-field slit probes. The particular type of the radiation source 406 and arrangement with the sensor elements 404A-404K in the array 416 will depend upon the specific application.

Figure 4B:
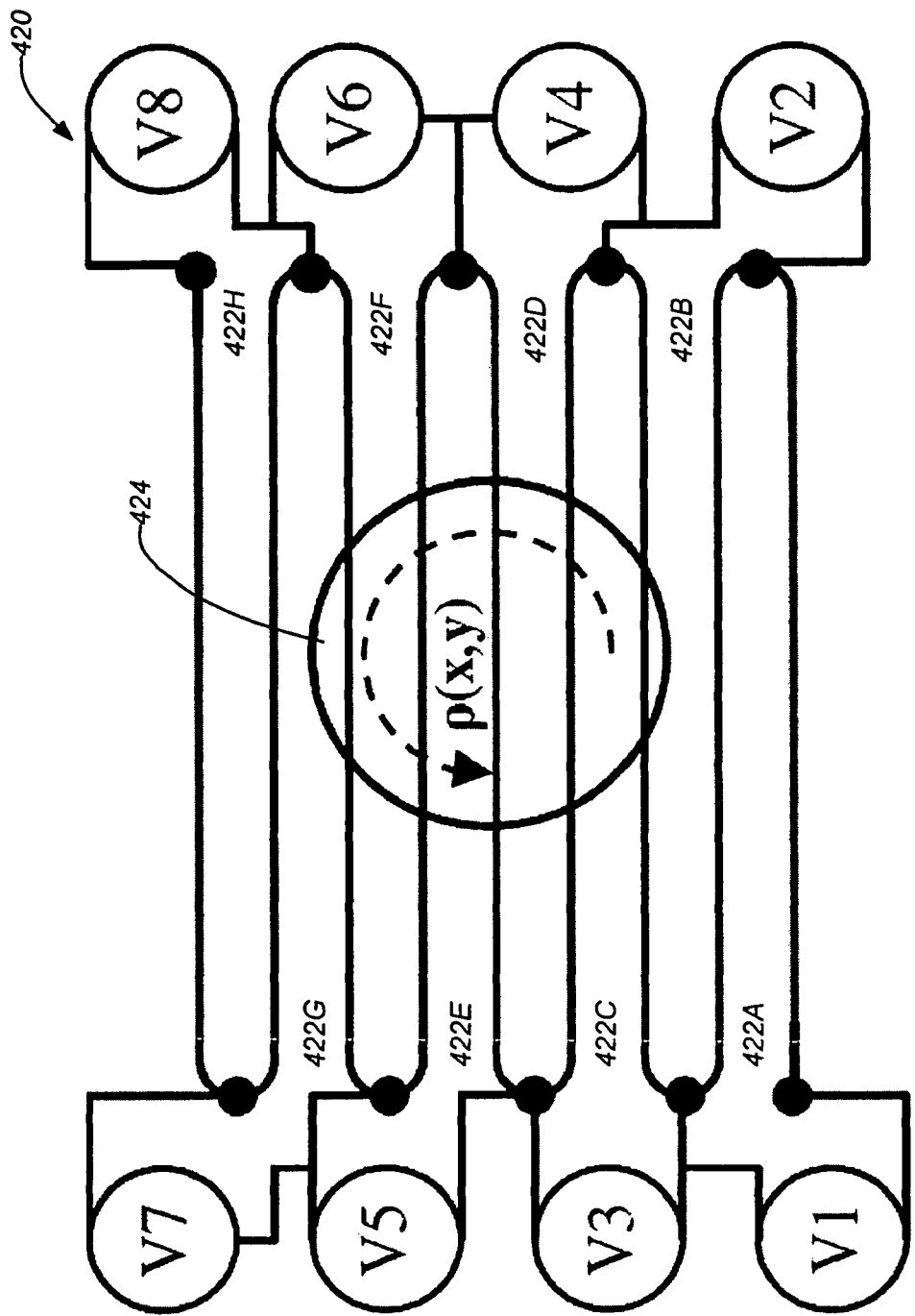
FIG. 4B illustrates an example embodiment of the invention comprising a stripe sensor array of inductive sensor elements.

FIG. 4B illustrates an example embodiment of the invention comprising a stripe sensor array 420 of inductive sensor elements 422A-422H. In this example, the technique as diagrammatically described in FIG. 4B, employs the example stripe sensor element of the stripe-type inductive detector loops as the elements 422A-422H which are sensed by voltages V1-V8, respectively. By creating a meander-like loop array disposed over a sample 424, and sequentially detecting voltages at nodes in the array as shown in FIG. 4B, sensing signals are obtained. As previously mentioned, employing a sequentially sensed array of stripe sensor elements in this manners eliminates the requirement for linear translation of the sample or the sensor element array as would be required with a single stripe sensor element. One notable advantage of the inductive sensor element array, e.g. constructed as shown in the FIG. 4B, is that each single conductor in the array (that has adjacent conductors on both sides) is used in two detector loops. For example, the second wire from the bottom in the FIG. 4B is part of the loop sensing V1 and part of the loop sensing V2. This arrangement minimizes the number of wires required in the array, improves the imaging resolution, simplifies the setup, and potentially reduces the imaging time as well. Each one-dimensional projection scan signal is generated by sequentially sensing the V1 to V8 at a distinct angle relative to the sample 424 to be imaged. Processing of the one-dimensional projection scan signals generated from the array 420 may be performed in the same manner as the apparatus 400 of FIG. 4A as will be understood by those skilled in the art.

Figure 5A:
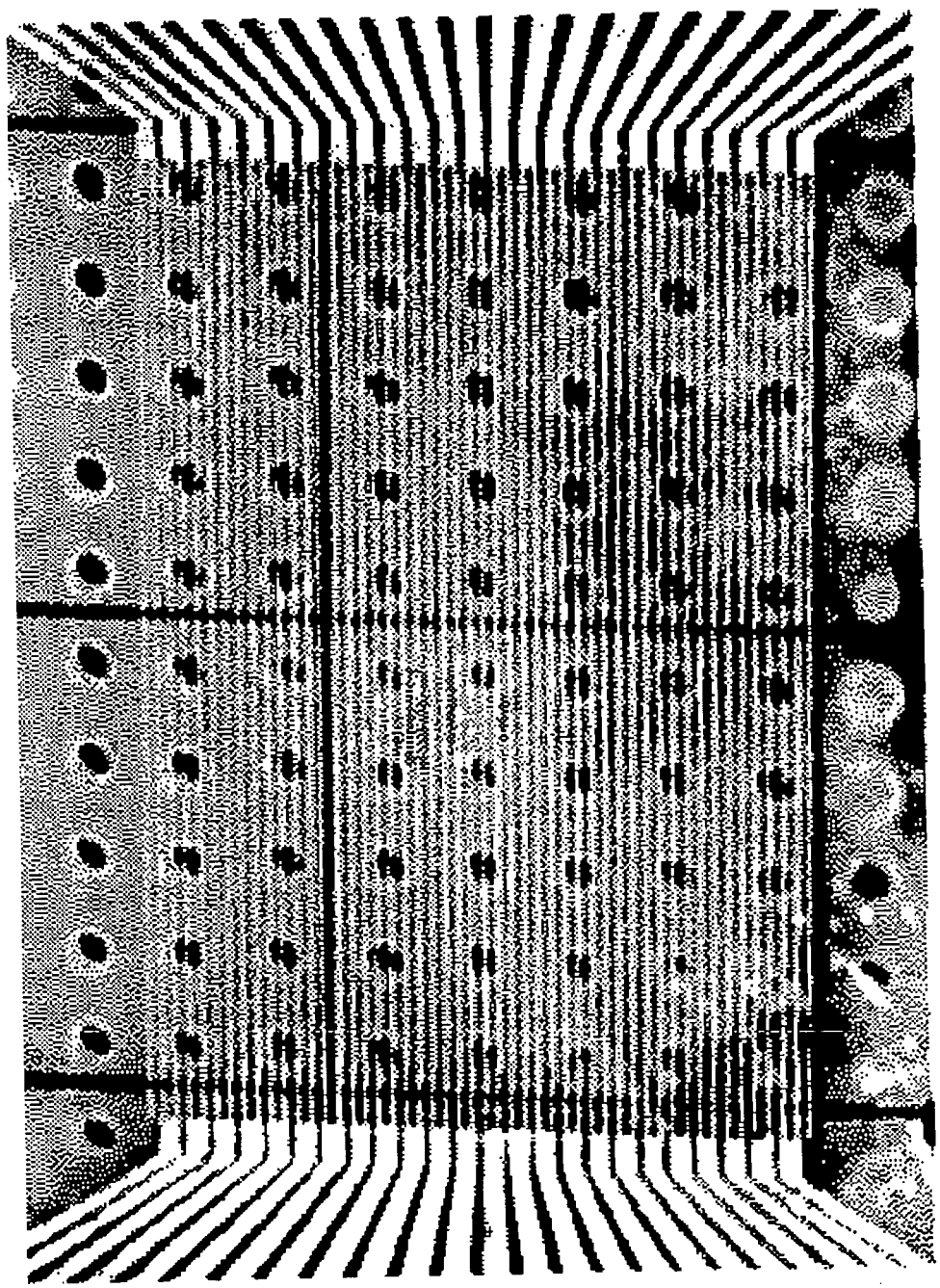
FIG. 5A illustrates an example embodiment of a sensor array prepared with conventional optical lithography techniques.

FIG. 5A illustrates an example embodiment of a sensor array prepared with conventional optical lithography techniques. The array comprises 50 Cr/Au wires approximately 50 μm wide, 100 nm thick, and separated by a center-to-center distance of 400 μm on a glass substrate for fifty detection loops. Wider wires may be used to connect the individual sensor elements of the array and fan out for easy contact access. An example sample is a two point circular coil pair mounted on a rotation stage (similar to the prior single stripe sensor element example), electrically arranged so that the ac currents in them are 180° out of phase. The data are collected sequentially from each loop of the array using the same source/audio power amplifier and transformer preamplifier/ lock-in amplifier arrangement, but this time without any linear translation. After all the loop voltage signals are recorded in sequence for a single angle, the sample is rotated by 10°, and procedure repeated.

Figure 5B:
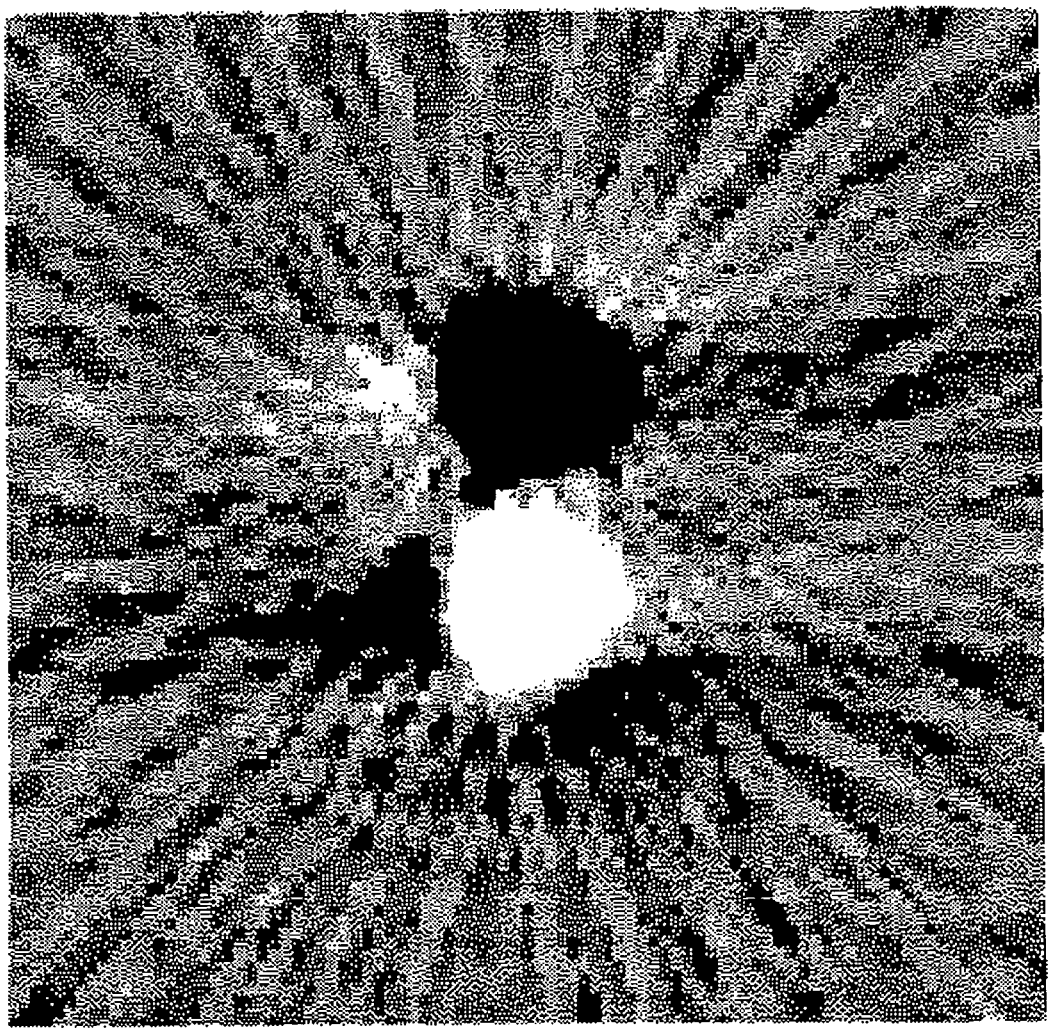
FIG. 5B shows a resulting image, reconstructed using the applied algorithm of Equation (2) employing the sensor array of FIG. 5A.

FIG. 5B shows a resulting image, reconstructed using the algorithm of Equation (2) employing the sensor array of FIG. 5A. Again, the test image is demonstrated by imaging of the two point sources with two-dimensional resolution limited only by the narrower thickness parameter of the sensor.

4. Stripe Sensor Versus Point Sensor Raster Imaging

Figure 6A:
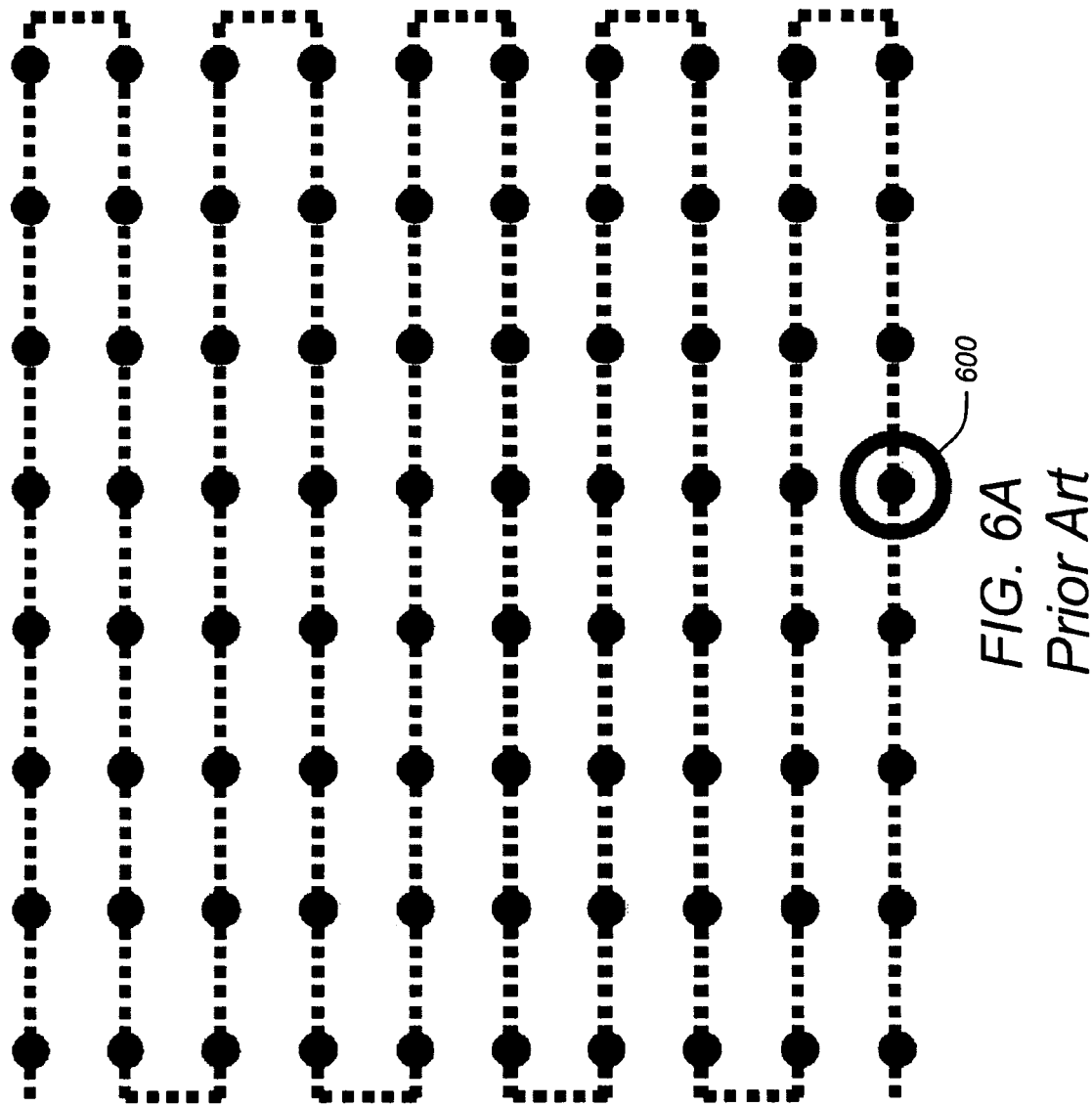
FIG. 6A illustrates an example conventional point-by-point rastering imaging process.

FIG. 6A illustrates an example conventional point-by-point rastering imaging process. In this section, some of the differences and consequences of stripe-type sensor imaging, e.g. as shown in FIG. 1B, compared to a conventional raster scanning point probe imaging, e.g., as shown in FIG. 6A, to better illustrate features of embodiments of the invention. Although both imaging methodologies, the raster scanning point-by-point imaging and stripe sensor imaging, provide two-dimensional images with resolution limited by the smaller parameter of the sensor, i.e., the thickness of the stripe sensor and size of the point sensor, respectively, there are several differences. Those skilled in the art will appreciate that although an inductive pickup loop detector is discussed in this example, similar analysis may be applied to other analogous sensor types.

One distinction is in the measurement time and consequently the signal-to-noise ratio of the two methodologies. In the raster scanning point probe method of FIG. 6A, the point probe 600 measures and resolves each pixel of the image individually for a certain measurement time T and only once during the course of the N×N step imaging sequence, e.g. along the dotted path. In contrast, for the stripe sensor element imaging mode, e.g. of FIG. 1B, the sensor detects multiple pixels of the image for a certain measurement time T at each step of the N steps linear scan and does not resolve the pixels along the sensor width. Nevertheless, through M angular orientations of the linear scans, as previously described, it still obtains the two-dimensional imaging with resolution defined by the thickness of the sensor only.

However, note that each pixel of the image in the stripe sensor element imaging technique may be detected by the sensor for every angular orientation of the linear scan, and is therefore detected M times. How this affects the signal to noise ratio (SNR) may be difficult to precisely estimate, although M times more measurements of each image pixel in the stripe sensor technique should provide the square root of M times better SNR. However, the larger length of the striped-shaped inductive loop sensor results in the larger sensor resistance R, and therefore larger RMS noise of the sensor which scales as the square root of R.

There is also a slight difference in the depth of view between the two imaging modalities (raster point scanning versus stripe element scanning) for the case of an inductive sensor. Using the principle of reciprocity, often used in the theory and practice of magnetic resonance and magnetic recording for signal reception analysis, the field patterns of the two methods may be compared to estimate the relative z-axis dependence of sensitivity between the two sensor shapes. See, e.g., W. F. Brown, Jr., Magnetostatic Principles in Ferromagnetism, North-Holland, Amsterdam, 1962; D. I. Hoult and R. E. Richards, J. Magn. Reson. 24, 71 1976; D. I. Hoult and P. C. Lauterbur, J. Magn. Reson. 34, 425 1979; and S. X. Wang and A. M. Taratorin, Magnetic Information Storage Technology Academic, San Diego, 1999, which are incorporated by reference herein.

Figure 6B:
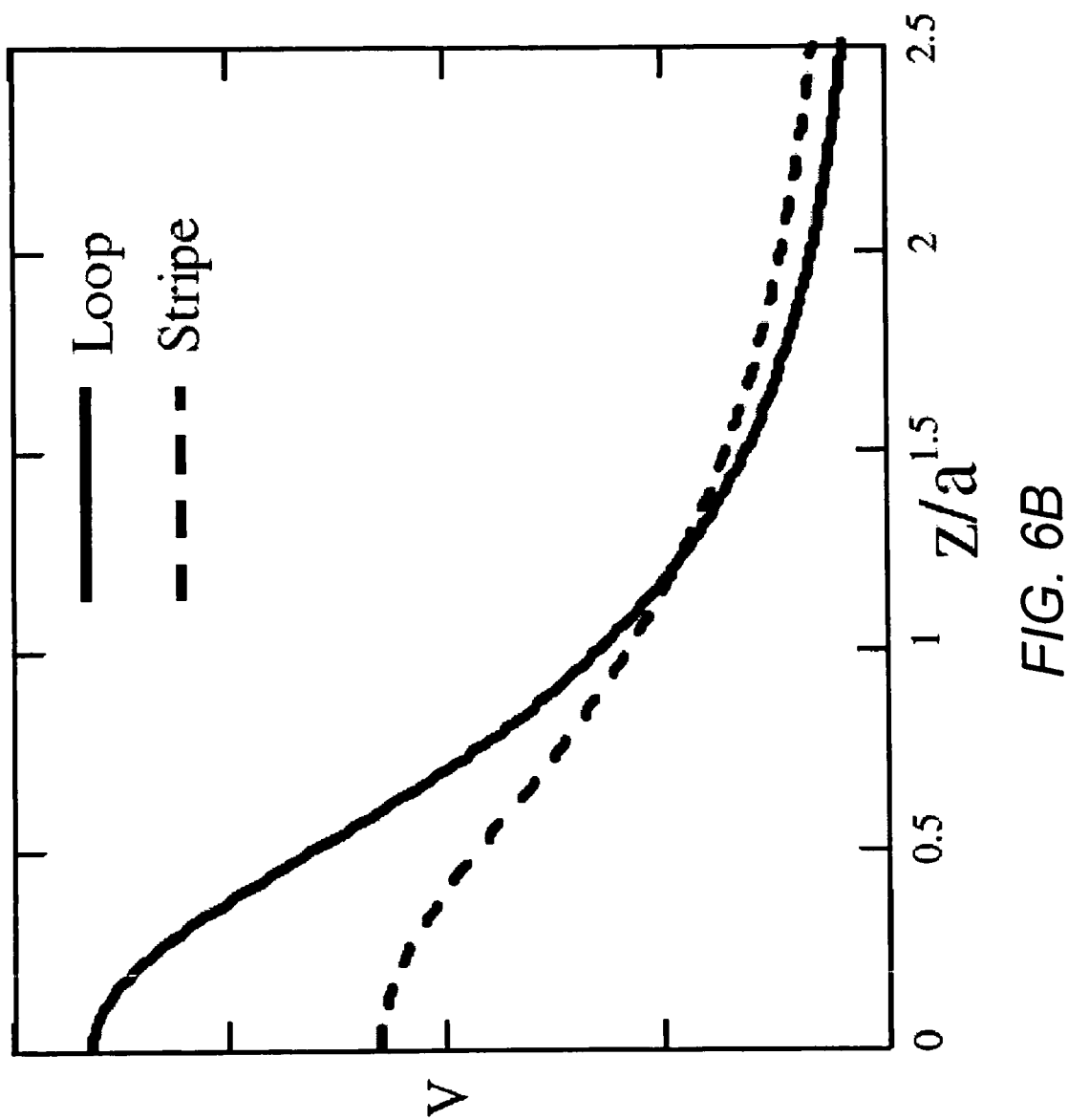
FIG. 6B shows the difference between the sensor sensitivity for an example inductive stripe sensor element and a point sensor element as a function of the sample distance along the z axis (perpendicular to the sample surface)

FIG. 6B shows the difference between the sensor sensitivity for an example inductive stripe sensor element and a point sensor element as a function of the sample distance along the z axis (perpendicular to the sample surface). For the inductive stripe sensor element example with wires of the stripe loop separated by distance $2a$ as compared to the circular loop of radius a, the graph indicates that the circular loop is more sensitive for the region of the sample close to the sensor, while the stripe loop is more sensitive for the region of the sample that is further away from the sensor. Therefore, the stripe sensor has a larger "depth of view" and weaker depth dependence of the received signal, while the point sensor is more sensitive at the surface of the sample and has steeper depth dependence of reception. The crossover point for sensitivity is at $z=1.21a$.

It should also be noted that, as related to potential use in MRI, a vertical field gradient could be employed for extending the imaging process to three dimensions. However, the signal from spins that are over a given stripe detector in the array start to significantly contribute to the signals being detected by neighboring stripe detectors. Therefore, spatial resolution may suffer further away from the detector array.

A comparison can also be made between the N-stripe array sensor described in FIGS. 4 and 5 and the N×N point sensors array used, for example, in the detection of biomedically related magnetic fields. See, The SQUID Handbook, edited by J. Clarke and A. I. Braginski, Wiley-VCH, Berlin, 2006, which is incorporated by reference herein. Again, both methods, in principle, achieve similar two-dimensional spatial imaging resolution. The stripe sensor array needs N times fewer sensors but requires sample (or array) rotation and tomographic computer reconstruction, while the N×N point sensor array does not require mechanical motion, but requires N times more detection channels for two-dimensional image acquisition.

There are two additional challenges that are present in the stripe sensor tomography described. Flat surface of the sample is one major restriction. This limitation is typically not an issue in point sensor scanning probe microscopy, where surface topography is obtained along with any other parameter of the sample (electrostatic, magnetic, etc.). Additionally, stripe sensor element tomography requires substantial uniformity of the sensor sensitivity response along the width of the sensor. This is well satisfied for the example inductive stripe sensor element presented, but implementation may be more problematic in, for example, a magnetoresistive stripe sensor element, where slight variation in the point sensitivity function along the sensor length has been experimentally observed. See, G. A. Gibson, S. Schultz, T. Carr, and T. Jagielinski, IEEE Trans. Magn., 28, 2310, 1992; and M. Todorovic and S. Schultz, J. Appl. Phys. 83, 6229, 1998, which are incorporated by reference herein.

5. Stripe Sensor Element Tomographic Imaging Applications

As previously mentioned, there are many other sensor families that may be suitable for stripe sensor tomographic implementation as will be understood by those skilled in the art. For example, thin film magneto-resistive sensors, asymmetric superconducting quantum interference devices (SQUIDs), elongated microfabricated waveguides and striplines, and nanoparticle-tape-filled microcoils used in NMR detection, planar asymmetric micro-Hall detectors, and microwave near-field slit probes as suitable candidates. Another possibility is the extension of the stripe array sensor idea into the submicron MRI resolution regime. See, M. Todorovic and S. Schultz, J. Appl. Phys. 83, 6229, 1998; S.-J. Kim, J. Chen, K. Nakajima, T. Yamashita, S. Takahashi, and T. Hatano, J. Appl. Phys. 91, 8495, 2002; Y. Maguire, I. L. Chuang, S. Zhang, and N. Gershenfeld, Proc. Natl. Acad. Sci.

U.S.A. 104, 9198, 2007; P. J. M. van Bentum, J. W. G. Janssen, A. P. M. Kentgens, J. Bart and J. G. E. Gardeniers, J. Magn. Reson. 189, 104, 2007; M. Barbic and A. Scherer, Solid State Nucl. Magn. Reson. 28, 91, 2005; H. Guillou, A. D. Kent, G. W. Stupian, and M. S. Leung, J. Appl. Phys., 93, 2746, 2003; F. Sakran, A. Copty, M. Golosovsky, N. Bontemps, D. Davidov, and A. Frankel, Appl. Phys. Lett. 82, 1479, 2003; and F. Sakran, A. Copty, M. Golosovsky, D. Davidov, and P. Monod, Appl. Phys. Lett. 84, 4499, 2004, which are incorporated by reference herein.

Figure 7:
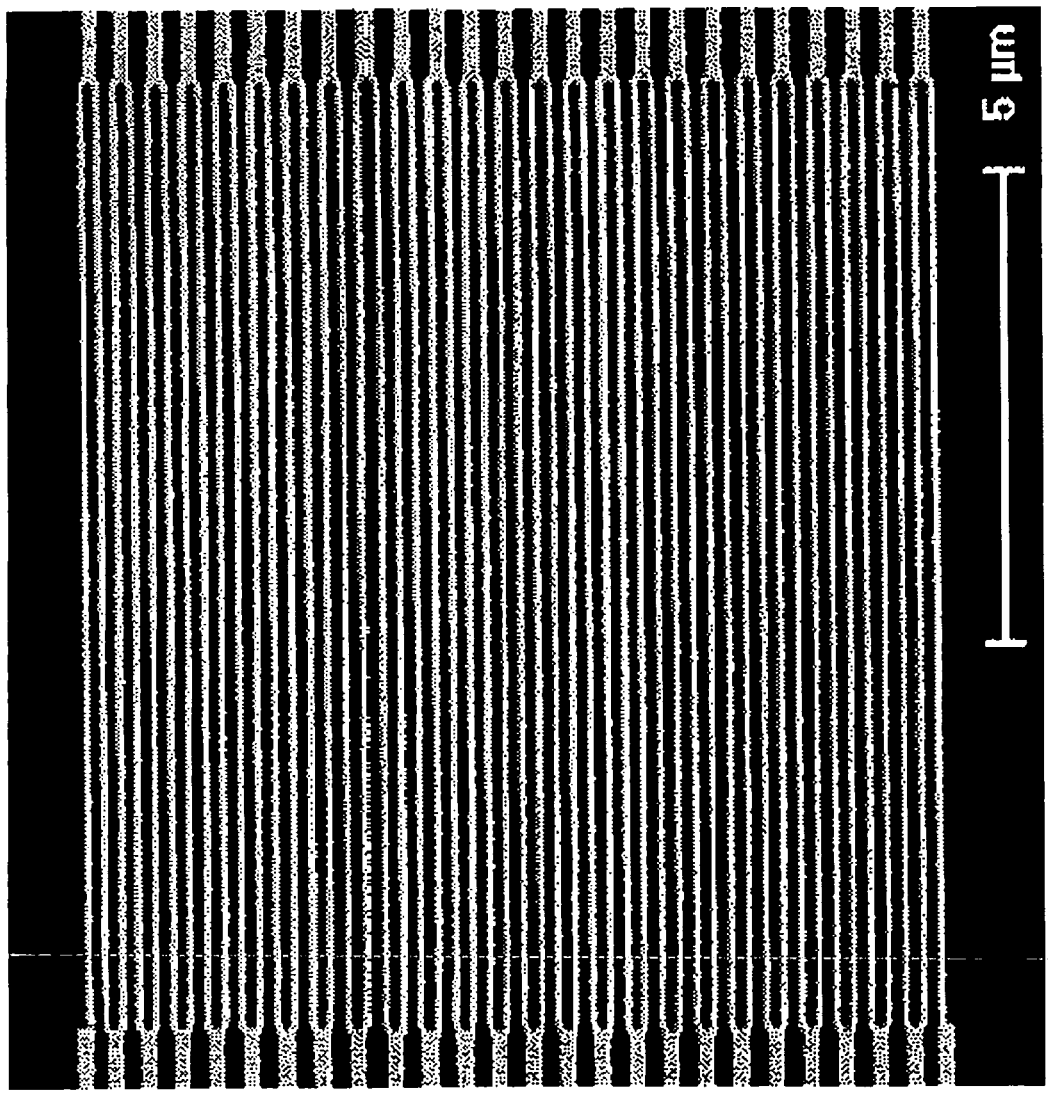
FIG. 7 illustrates a nanofabricated version of an example inductive loop sensor array in accordance with an embodiment of the invention.

FIG. 7 illustrates a nanofabricated version of an example inductive loop sensor array. In this regime, the flatness of the sample and the requirement for angular rotation of the sample may prove especially difficult. However, electro-rotation of samples may provide one viable solution to the nanoscale angular orientation challenge as will be understood by those skilled in the art. Although such miniaturized conductor structures exhibit increased resistance and therefore may degrade SNR of an inductive detector, they also provide a higher field per unit current, $B_1/I$, at the sample location. Careful and extensive analysis of SNR of microcoil structures in NMR detection indicates that SNR per unit volume increases as the inductive detector decreases in size, further motivating size reduction of the inductive stripe sensor array. It is also interesting that in potential magnetic resonance imaging implementation on this size scale, the technique would operate in the regime where nuclear spin noise signal is appreciable and comparable to the conventional NMR signal. Therefore, two-dimensional imaging with a submicron stripe sensor array in that case may be performed without the need for external imaging gradient fields and without the need for high power radio-frequency excitation. See, W. M. Arnold and U. Zimmermann, J. Electrost. 21, 151, 1988; T. L. Peck, R. L. Magin, and P. C. Lauterbur, J. Magn. Reson., Ser. B 108, 114, 1995; A. G. Webb, Prog. Nucl. Magn. Reson. Spectrosc. 31, 1, 1997; and N. Muller and A. Jerschow, Proc. Natl. Acad. Sci. U.S.A. 103, 6790, 2006, which are incorporated by reference herein.

6. Method of Tomographic Imaging

Figure 8A:
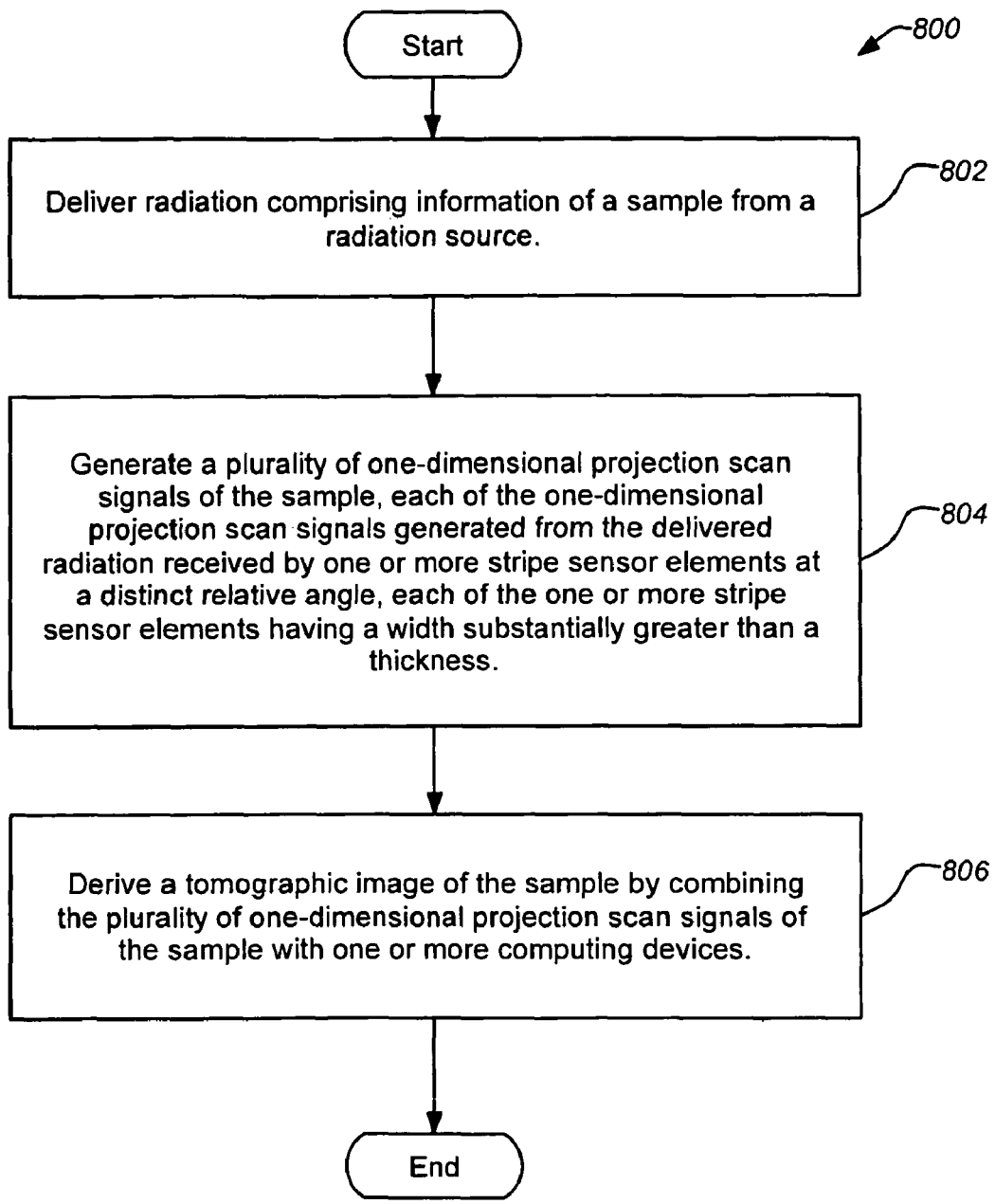
FIG. 8A is a flowchart of an exemplary method of tomographic imaging.

FIG. 8A is a flowchart of an exemplary method 800 of tomographic imaging. The method 800 begins with an operation 802 of directing radiation comprising information of a sample from a radiation source. Next in operation 804 a plurality of one-dimensional projection scan signals of the sample are generated, each of the one-dimensional projection scan signals generated from the directed radiation received by one or more stripe sensor elements at a distinct relative angle and each of the one or more stripe sensor elements having a width substantially greater than a thickness. Finally, in operation 806 a tomographic image of the sample is derived by combining the plurality of one-dimensional projection scan signals of the sample with one or more computing devices. The method 800 may be further modified consistent with the apparatuses and examples previously described. For example, the method 800 may be further defined through specific sub-operations for deriving the tomographic image by combining the plurality of one-dimensional projection scan signals of the sample.

Figure 8B:
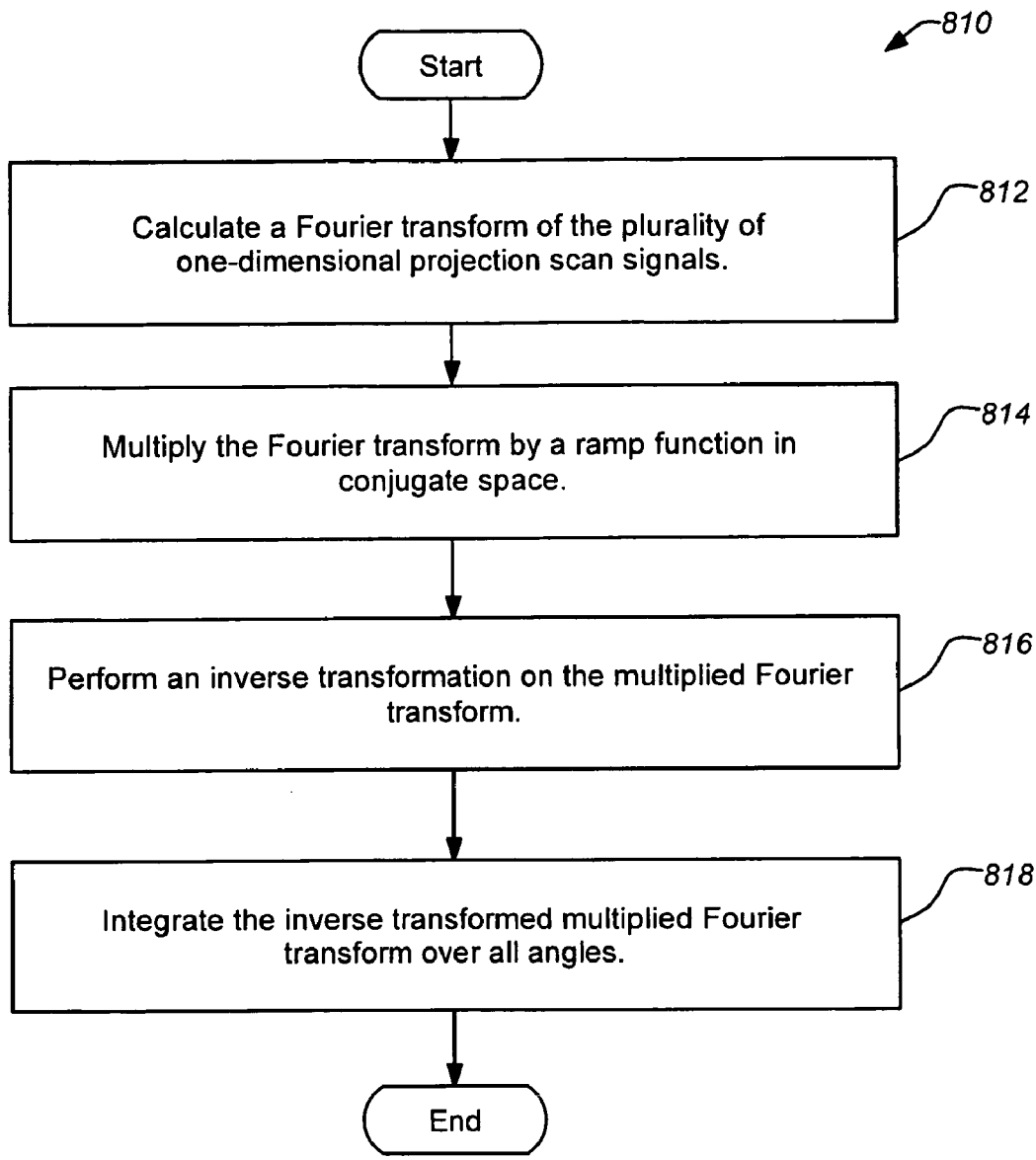
FIG. 8B is a flowchart of a sub-method for deriving the tomographic image by combining the plurality of one-dimensional projection scan signals of the sample.

FIG. 8B is a flowchart of a sub-method 810 for deriving the tomographic image by combining the plurality of one-dimensional projection scan signals of the sample. The sub-method 810 begins by an operation 812 of calculating a Fourier transform of the plurality of one-dimensional projection scan signals. Next in operation 814 the Fourier transform is multiplied by a ramp function in conjugate space. Following this, an inverse transformation is performed on the multiplied Fourier transform in operation 816. Finally in operation 818 the inverse transformed multiplied Fourier transform is integrated over all angles.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. An apparatus, comprising:
   a radiation source for delivering radiation comprising information of a sample;
   one or more stripe sensor elements, each having a width substantially greater than a thickness, for generating a plurality of one-dimensional projection scan signals of the sample, each of the one-dimensional projection scan signals generated from the directed radiation received by the one or more stripe sensor elements at a distinct relative angle; and
   one or more computing devices for deriving a tomographic image of the sample by combining the plurality of one-dimensional projection scan signals of the sample.

2. The apparatus of claim 1, wherein deriving the tomographic image of the sample comprises calculating a Fourier transform of the plurality of one-dimensional projection scan signals, multiplication by a ramp function in conjugate space followed by an inverse transformation, and finally integration over all angles.

3. The apparatus of claim 1, wherein the received radiation comprises the information of the sample by reflection from the radiation source off the sample.

4. The apparatus of claim 1, wherein the received radiation comprises the information of the sample by transmission from the radiation source across the sample.

5. The apparatus of claim 1, wherein the received radiation comprises the information of the sample by emission where the sample comprises the radiation source itself.

6. The apparatus of claim 1, wherein the one or more stripe sensor elements are scanned linearly across the sample at each distinct relative angle to generate each of the plurality of one-dimensional scan signals of the sample.

7. The apparatus of claim 1, wherein the one or more stripe sensor elements each provide substantially equal sensitivity along the width.

8. The apparatus of claim 1, wherein the one or more stripe sensor elements each comprise an elongated inductive coil loop including two substantially parallel conductors.

9. The apparatus of claim 1, wherein the one or more stripe sensor elements are selected from the group comprising thin film magneto-resistive sensors, asymmetric superconducting interference devices (SQUIDS), nuclear magnetic resonance (NMR) elongated micro-fabricated waveguides and stripelines, planar asymmetric micro-Hall detectors and microwave near-field slit probes.

10. The apparatus of claim 1, wherein the one or more stripe sensor elements comprises a plurality of adjacent stripe sensor elements in a linear array each adjacent along the width.

11. The apparatus of claim 10, wherein each of the plurality of the one-dimensional projection scan signals is generated by sequentially sensing the plurality of adjacent stripe sensor elements at the distinct relative angle.

12. The apparatus of claim 10, wherein each of the plurality of adjacent stripe sensor elements of the linear array comprise an elongated inductive coil loop including two substantially parallel conductors and the adjacent stripe sensor elements share a common conductor of the two substantially parallel conductors.

13. A method, comprising the steps of:
directing radiation comprising information of a sample from a radiation source;
generating a plurality of one-dimensional projection scan signals of the sample, each of the one-dimensional projection scan signals generated from the directed radiation received by one or more stripe sensor elements at a distinct relative angle, each of the one or more stripe sensor elements having a width substantially greater than a thickness; and
deriving a tomographic image of the sample by combining the plurality of one-dimensional projection scan signals of the sample with one or more computing devices.

14. The method of claim 13, wherein deriving the tomographic image of the sample comprises:
calculating a Fourier transform of the plurality of one-dimensional projection scan signals;
multiplying the Fourier transform by a ramp function in conjugate space;
performing an inverse transformation on the multiplied Fourier transform; and
integrating the inverse transformed multiplied Fourier transform over all angles.

15. The method of claim 13, wherein directing the radiation comprises reflecting the radiation from the radiation source off the sample such that the received radiation comprises the information of the sample.

16. The method of claim 13, wherein directing the radiation comprises transmitting the radiation from the radiation source across the sample such that the received radiation comprises the information of the sample.

17. The method of claim 13, wherein directing the radiation comprises emitting the radiation from the sample such that received radiation from the sample itself comprises the information of the sample.

18. The method of claim 13, further comprising scanning the one or more stripe sensor elements linearly across the sample at each distinct relative angle to generate each of the plurality of one-dimensional scan signals of the sample.

19. The method of claim 13, wherein the one or more stripe sensor elements each provide substantially equal sensitivity along the width.

20. The method of claim 13, wherein the one or more stripe sensor elements each comprise an elongated inductive coil loop including two substantially parallel conductors.

21. The method of claim 13, wherein the one or more stripe sensor elements are selected from the group comprising thin film magneto-resistive sensors, asymmetric superconducting interference devices (SQUIDS), nuclear magnetic resonance (NMR) elongated micro-fabricated waveguides and stripe-lines, planar asymmetric micro-Hall detectors and microwave near-field slit probes.

22. The method of claim 13, wherein the one or more stripe sensor elements comprises a plurality of adjacent stripe sensor elements in a linear array each adjacent along the width.

23. The method of claim 22, wherein generating the plurality of one-dimensional projection scan signals of the sample comprises sequentially sensing each of the plurality of the one-dimensional projection scan signals from the plurality of adjacent stripe sensor elements at the distinct relative angle.

24. The method of claim 22, wherein each of the plurality of adjacent stripe sensor elements of the linear array comprise an elongated inductive coil loop including two substantially parallel conductors and the adjacent stripe sensor elements share a common conductor of the two substantially parallel conductors.

25. An apparatus, comprising:
a radiation source means for directing radiation comprising information of a sample;
one or more stripe sensor element means, each having a width substantially greater than a thickness, for generating a plurality of one-dimensional projection scan signals of the sample, each of the one-dimensional projection scan signals generated from the directed radiation received by the one or more stripe sensor element means at a distinct relative angle; and
one or more computing device means for deriving a tomographic image of the sample by combining the plurality of one-dimensional projection scan signals of the sample.

26. The apparatus of claim 25, wherein the one or more stripe sensor element means are scanned linearly across the sample at each distinct relative angle to generate each of the plurality of one-dimensional scan signals of the sample.

27. The apparatus of claim 25, wherein the one or more stripe sensor element means comprise a plurality of adjacent stripe sensor elements in a linear array each adjacent along the width and each of the plurality of the one-dimensional projection scan signals is generated by sequentially sensing the plurality of adjacent stripe sensor elements at the distinct relative angle.

28. The apparatus of claim 25, wherein deriving the tomographic image of the sample comprises calculating a Fourier transform of the plurality of one-dimensional projection scan signals, multiplication by a ramp function in conjugate space followed by an inverse transformation, and finally integration over all angles.

* * * * *